(12) United States Patent
Harrison (10) Patent No.: US 9,675,757 B2
(45) Date of Patent: *Jun. 13, 2017

(54) INJECTION DEVICE (75) Inventor: Nigel Harrison, Melbourn (GB)

(73) Assignee: Cilag gmBh International (CH)

( * ) Notice: Subject to any disclaimer, the term of this patent is extended or adjusted under 35 U.S.C. 154(b) by 2213 days.

This patent is subject to a terminal disclaimer.

(21) Appl. No.: 11/579,360

(22) PCT Filed: May 27, 2005

(86) PCT No.: PCT/GB2005/002105
§ 371 (c)(1),
(2), (4) Date: Aug. 28, 2008

(87) PCT Pub. No.: WO2005/115506
PCT Pub. Date: Dec. 8, 2005

(65) Prior Publication Data
US 2008/0312591 A1    Dec. 18, 2008

(30) Foreign Application Priority Data

May 28, 2004    (GB) ................................. 0412050.7

(51) Int. Cl.
*A61M 5/20*   (2006.01)
*A61M 5/32*   (2006.01)
*A61M 5/24*   (2006.01)

(52) U.S. Cl.
CPC ............. *A61M 5/2033* (2013.01); *A61M 5/24* (2013.01); *A61M 5/3204* (2013.01); *A61M 5/326* (2013.01);
(Continued)

(58) Field of Classification Search
CPC ................ A61M 5/2033; A61M 5/326; A61M 2005/2086; A61M 2005/206
(Continued)

(56) References Cited

U.S. PATENT DOCUMENTS 1,845,036 A    2/1932   Busher
2,019,382 A    10/1935  Aronson
(Continued)

FOREIGN PATENT DOCUMENTS

CH    518102 A    1/1972
CN    229932 A1   11/1985
(Continued)

OTHER PUBLICATIONS

European Search Report dated Aug. 3, 2011; Application No. 11170040.
(Continued)

*Primary Examiner* — Matthew F Desanto (57) ABSTRACT

An injection device (210) is described. A housing (212) receives a syringe and includes a return spring (226) for biasing the syringe from an extended position in which its needle (218) extends from the housing (212) to a retracted position in which the it does not. A drive spring (230) acts on a first drive element (232) and a second drive element (234) acts upon the syringe to advance it from its retracted position to its extended position and discharge its contents through the needle. The first drive element (232) is capable of movement relative to the second (234) once a nominal decoupling position has been reached. A release mechanism is activated when the first drive element (234) is further advanced to a nominal release position, to release the syringe (214) from the action of the drive spring (230), whereupon the return spring (226) restores the syringe (214) to its retracted position. Decoupling of the drive elements is achieved with a particular form of releasable drive coupling using two pairs of overlying flexible arms (235, 247). A particular form of release mechanism that also uses flexible arms (233) is also envisaged.

30 Claims, 2 Drawing Sheets (52) U.S. Cl.
CPC . *A61M 2005/202* (2013.01); *A61M 2005/206* (2013.01); *A61M 2005/3261* (2013.01)

(58) Field of Classification Search
USPC ... 604/110, 136, 131–135, 192–198, 263, 68
See application file for complete search history.

(56) References Cited

U.S. PATENT DOCUMENTS

| | | |
|---|---|---|
| 2,147,616 A | 2/1939 | Chaput |
| 2,295,849 A | 9/1942 | Kayden |
| 2,531,267 A | 11/1950 | Harisch |
| 2,764,977 A | 10/1956 | Ferguson |
| 2,828,742 A | 4/1958 | Ashkenaz |
| 2,854,975 A | 10/1958 | Cohen |
| 3,076,455 A | 2/1963 | McConnaughey et al. |
| 3,131,692 A | 5/1964 | Love |
| 3,320,955 A | 5/1967 | Sarnoff |
| 3,329,146 A | 7/1967 | Waldman |
| 3,543,603 A | 12/1970 | Gley |
| 3,656,472 A | 4/1972 | Moura |
| 3,702,608 A | 11/1972 | Tibbs |
| 3,742,948 A | 7/1973 | Post et al. |
| 3,797,488 A | 3/1974 | Hurschman et al. |
| 3,797,489 A | 3/1974 | Sarnoff |
| 3,880,163 A | 4/1975 | Ritterskamp |
| 3,976,069 A | 8/1976 | Ong |
| 4,165,739 A | 8/1979 | Doherty et al. |
| 4,180,070 A | 12/1979 | Genese |
| 4,185,628 A | 1/1980 | Kopfer |
| 4,194,505 A | 3/1980 | Schmitz |
| 4,222,380 A | 9/1980 | Terayama |
| 4,231,368 A | 11/1980 | Becker |
| 4,236,516 A | 12/1980 | Nilson |
| 4,237,882 A | 12/1980 | Wickham |
| 4,299,238 A | 11/1981 | Baidwan et al. |
| 4,333,459 A | 6/1982 | Becker |
| 4,378,015 A | 3/1983 | Wardlaw |
| 4,394,863 A | 7/1983 | Bartner |
| 4,403,989 A | 9/1983 | Christensen et al. |
| 4,407,283 A | 10/1983 | Reynolds |
| 4,425,120 A | 1/1984 | Sampson et al. |
| 4,430,082 A | 2/1984 | Schwabacher |
| 4,521,237 A | 6/1985 | Logothetis |
| 4,561,856 A | 12/1985 | Cochran et al. |
| 4,627,835 A | 12/1986 | Fenton, Jr. |
| 4,636,201 A | 1/1987 | Ambrose et al. |
| 4,639,250 A | 1/1987 | Rycroft |
| 4,642,099 A | 2/1987 | Phillips et al. |
| 4,676,530 A | 6/1987 | Nordgren et al. |
| 4,717,383 A | 1/1988 | Phillips et al. |
| 4,744,786 A | 5/1988 | Hooven et al. |
| 4,787,891 A | 11/1988 | Levin et al. |
| 4,874,383 A | 10/1989 | McNaughton |
| 4,874,384 A | 10/1989 | Nunez |
| 4,929,232 A | 5/1990 | Sweeney et al. |
| 4,969,870 A | 11/1990 | Kramer et al. |
| 4,988,339 A | 1/1991 | Vadher |
| 5,009,646 A | 4/1991 | Sudo et al. |
| 5,026,349 A | 6/1991 | Schmitz et al. |
| 5,057,079 A | 10/1991 | Tiemann et al. |
| 5,092,842 A | 3/1992 | Bechtold et al. |
| 5,098,400 A | 3/1992 | Crouse et al. |
| 5,112,119 A | 5/1992 | Cooke et al. |
| 5,114,406 A | 5/1992 | Gabriel et al. |
| 5,122,119 A | 6/1992 | Lucas |
| 5,137,516 A | 8/1992 | Rand et al. |
| 5,141,496 A | 8/1992 | Dalto et al. |
| 5,147,325 A | 9/1992 | Mitchell et al. |
| 5,156,599 A | 10/1992 | Ranford et al. |
| 5,176,643 A | 1/1993 | Kramer et al. |
| 5,190,526 A | 3/1993 | Murray et al. |
| 5,242,416 A | 9/1993 | Hutson |
| 5,250,026 A | 10/1993 | Ehrlich et al. |
| 5,250,037 A | 10/1993 | Bitdinger |
| 5,263,933 A | 11/1993 | Novacek et al. |
| 5,267,963 A | 12/1993 | Bachynsky |
| 5,271,744 A | 12/1993 | Kramer et al. |
| 5,295,965 A | 3/1994 | Wilmot |
| 5,300,030 A | 4/1994 | Crossman et al. |
| 5,312,364 A | 5/1994 | Jacobs |
| 5,330,081 A | 7/1994 | Davenport |
| 5,330,430 A | 7/1994 | Sullivan |
| 5,356,395 A | 10/1994 | Chen |
| 5,358,489 A | 10/1994 | Wyrick |
| 5,364,369 A | 11/1994 | Reynolds |
| 5,368,577 A | 11/1994 | Teoh et al. |
| 5,372,586 A | 12/1994 | Haber et al. |
| 5,391,151 A | 2/1995 | Wilmot |
| 5,405,362 A | 4/1995 | Kramer et al. |
| 5,411,488 A | 5/1995 | Pagay et al. |
| 5,425,715 A | 6/1995 | Dalling et al. |
| 5,451,210 A | 9/1995 | Kramer et al. |
| 5,478,316 A | 12/1995 | Bitdinger et al. |
| 5,480,387 A | 1/1996 | Gabriel et al. |
| 5,487,732 A | 1/1996 | Jeffrey |
| 5,489,256 A | 2/1996 | Adair |
| 5,503,627 A | 4/1996 | McKinnon et al. |
| 5,514,097 A | 5/1996 | Knauer |
| 5,520,653 A | 5/1996 | Reilly et al. |
| 5,540,660 A | 7/1996 | Jenson et al. |
| 5,540,666 A | 7/1996 | Barta et al. |
| 5,540,709 A | 7/1996 | Ramel et al. |
| 5,567,160 A | 10/1996 | Massino |
| 5,569,191 A | 10/1996 | Meyer |
| 5,569,192 A | 10/1996 | van der Wal |
| 5,575,777 A | 11/1996 | Cover et al. |
| 5,599,302 A | 2/1997 | Lilley et al. |
| 5,599,309 A | 2/1997 | Marshall et al. |
| 5,607,395 A | 3/1997 | Ragsdale et al. |
| 5,609,577 A | 3/1997 | Haber et al. |
| 5,609,584 A | 3/1997 | Gettig et al. |
| 5,611,785 A | 3/1997 | Mito et al. |
| 5,637,094 A | 6/1997 | Stewart, Jr. et al. |
| 5,645,536 A | 7/1997 | Whisson |
| 5,647,845 A | 7/1997 | Haber et al. |
| 5,649,912 A | 7/1997 | Peterson |
| 5,658,259 A | 8/1997 | Pearson et al. |
| 5,665,071 A | 9/1997 | Wyrick |
| 5,681,291 A | 10/1997 | Galli |
| 5,697,908 A | 12/1997 | Imbert |
| 5,702,367 A | 12/1997 | Cover et al. |
| 5,704,911 A | 1/1998 | Parsons et al. |
| 5,709,662 A | 1/1998 | Olive et al. |
| 5,713,866 A | 2/1998 | Wilmot |
| 5,748,316 A | 5/1998 | Wakabayashi et al. |
| 5,779,668 A | 7/1998 | Grabenkort |
| 5,779,677 A | 7/1998 | Frezza |
| 5,807,334 A | 9/1998 | Hodosh et al. |
| 5,817,058 A | 10/1998 | Shaw |
| 5,827,262 A | 10/1998 | Neftel et al. |
| 5,843,036 A | 12/1998 | Olive et al. |
| 5,855,839 A | 1/1999 | Brunel |
| 5,865,795 A | 2/1999 | Schiff et al. |
| 5,865,804 A | 2/1999 | Bachynsky |
| 5,868,711 A | 2/1999 | Kramer et al. |
| 5,879,327 A | 3/1999 | Moreau DeFarges et al. |
| 5,913,843 A | 6/1999 | Jentzen |
| 5,928,205 A | 7/1999 | Marshall |
| 5,954,738 A | 9/1999 | LeVaughn et al. |
| 5,957,897 A | 9/1999 | Jeffrey |
| 5,960,797 A | 10/1999 | Kramer et al. |
| 5,997,513 A | 12/1999 | Smith et al. |
| 6,007,515 A | 12/1999 | Epstein et al. |
| 6,015,438 A | 1/2000 | Shaw |
| 6,017,330 A | 1/2000 | Hitchins et al. |
| 6,036,675 A | 3/2000 | Thorne et al. |
| 6,045,534 A | 4/2000 | Jacobsen et al. |
| 6,068,614 A | 5/2000 | Kimber et al. |
| 6,077,247 A | 6/2000 | Marshall et al. |
| 6,083,197 A | 7/2000 | Umbaugh |
| 6,086,562 A | 7/2000 | Jacobsen et al. |
| 6,090,070 A | 7/2000 | Hager et al. |
| 6,090,078 A | 7/2000 | Erskine |
| 6,090,897 A | 7/2000 | Akasaki et al. |

(56) References Cited

U.S. PATENT DOCUMENTS

| | | |
|---|---|---|
| 6,099,503 A * | 8/2000 | Stradella .................... 604/135 |
| 6,099,504 A | 8/2000 | Gross |
| 6,123,684 A | 9/2000 | Deboer et al. |
| 6,139,534 A | 10/2000 | Niedospial, Jr. et al. |
| 6,159,161 A | 12/2000 | Hodosh |
| 6,159,181 A | 12/2000 | Crossman et al. |
| 6,159,184 A | 12/2000 | Perez et al. |
| 6,162,199 A | 12/2000 | Geringer |
| 6,171,276 B1 | 1/2001 | Lippe et al. |
| 6,179,812 B1 | 1/2001 | Botich et al. |
| 6,186,980 B1 | 2/2001 | Brunel |
| 6,190,363 B1 | 2/2001 | Gabbard et al. |
| 6,193,696 B1 | 2/2001 | Jansen et al. |
| 6,203,530 B1 | 3/2001 | Stewart, Sr. |
| 6,209,738 B1 | 4/2001 | Jansen et al. |
| 6,221,044 B1 | 4/2001 | Grecco |
| 6,228,055 B1 | 5/2001 | Foerster et al. |
| 6,258,068 B1 | 7/2001 | Kirchhofer et al. |
| 6,270,479 B1 | 8/2001 | Bergens et al. |
| 6,280,421 B1 | 8/2001 | Kirchhofer et al. |
| 6,290,683 B1 | 9/2001 | Erez et al. |
| 6,293,925 B1 | 9/2001 | Safabash et al. |
| 6,317,939 B1 | 11/2001 | Malin |
| 6,330,960 B1 | 12/2001 | Faughey et al. |
| 6,332,875 B2 | 12/2001 | Inkpen et al. |
| 6,371,939 B2 | 4/2002 | Bergens et al. |
| 6,371,959 B1 | 4/2002 | Trice |
| 6,387,078 B1 | 5/2002 | Gillespie, III |
| 6,391,003 B1 | 5/2002 | Lesch, Jr. |
| 6,419,658 B1 | 7/2002 | Restelli et al. |
| 6,428,528 B2 | 8/2002 | Sadowski et al. |
| 6,447,480 B1 | 9/2002 | Brunel |
| 6,454,743 B1 | 9/2002 | Weber |
| 6,454,746 B1 | 9/2002 | Bydlon et al. |
| 6,461,333 B1 | 10/2002 | Frezza |
| 6,491,667 B1 | 12/2002 | Keane et al. |
| 6,517,517 B1 | 2/2003 | Farrugia et al. |
| 6,537,252 B1 | 3/2003 | Hansen |
| 6,544,234 B1 | 4/2003 | Gabriel |
| 6,565,540 B1 | 5/2003 | Perouse et al. |
| 6,565,553 B2 | 5/2003 | Sadowski et al. |
| 6,569,115 B1 | 5/2003 | Barker et al. |
| 6,569,123 B2 | 5/2003 | Alchas et al. |
| 6,569,124 B1 | 5/2003 | Perouse |
| 6,572,581 B1 | 6/2003 | Landau |
| 6,575,939 B1 | 6/2003 | Brunel |
| 6,585,702 B1 | 7/2003 | Brunel |
| 6,589,210 B1 | 7/2003 | Rolfe |
| 6,595,957 B1 | 7/2003 | Griffiths et al. |
| 6,595,962 B1 | 7/2003 | Perthu |
| 6,599,272 B1 | 7/2003 | Hjertman et al. |
| 6,607,508 B2 | 8/2003 | Knauer |
| 6,607,510 B2 | 8/2003 | Landau |
| 6,613,022 B1 | 9/2003 | Doyle |
| 6,620,137 B2 | 9/2003 | Kirchhofer et al. |
| 6,638,256 B2 | 10/2003 | Jansen et al. |
| 6,641,554 B2 | 11/2003 | Landau |
| 6,641,560 B1 | 11/2003 | Bechtold et al. |
| 6,641,565 B1 | 11/2003 | Lavi et al. |
| 6,645,170 B2 | 11/2003 | Landau |
| 6,645,181 B1 | 11/2003 | Lavi et al. |
| 6,648,835 B1 | 11/2003 | Shemesh |
| 6,648,850 B2 | 11/2003 | Landau |
| 6,656,163 B1 | 12/2003 | Marshall et al. |
| 6,673,049 B2 | 1/2004 | Hommann et al. |
| 6,676,630 B2 | 1/2004 | Landau et al. |
| 6,689,093 B2 | 2/2004 | Landau |
| 6,692,469 B1 | 2/2004 | Weekes et al. |
| 6,699,220 B2 | 3/2004 | Rolfe |
| 6,740,062 B2 | 5/2004 | Hjertman |
| 6,743,199 B2 | 6/2004 | Shue et al. |
| 6,743,203 B1 | 6/2004 | Pickhard et al. |
| 6,746,429 B2 | 6/2004 | Sadowski et al. |
| 6,746,438 B1 | 6/2004 | Arnissolle |
| 6,767,336 B1 | 7/2004 | Kaplan |
| 6,770,056 B2 | 8/2004 | Price et al. |
| 6,776,777 B2 | 8/2004 | Barrelle |
| 6,783,509 B1 | 8/2004 | Landau et al. |
| 6,793,161 B1 | 9/2004 | Fujita et al. |
| 6,796,967 B2 | 9/2004 | Jensen |
| 6,811,548 B2 | 11/2004 | Jeffrey |
| 6,817,987 B2 | 11/2004 | Vetter et al. |
| 6,846,303 B2 | 1/2005 | Eakins et al. |
| 6,875,205 B2 | 4/2005 | Leinsing |
| 6,890,319 B1 | 5/2005 | Crocker |
| 6,899,698 B2 | 5/2005 | Sams |
| 6,902,543 B1 | 6/2005 | Cherif-Cheikh et al. |
| 6,932,793 B1 | 8/2005 | Marshall et al. |
| 6,939,319 B1 | 9/2005 | Anstead et al. |
| 6,939,330 B1 | 9/2005 | McConnell et al. |
| 6,979,316 B1 | 12/2005 | Rubin et al. |
| 7,066,907 B2 | 6/2006 | Crossman et al. |
| 7,097,071 B2 | 8/2006 | Anderson et al. |
| 7,097,634 B2 | 8/2006 | Gilbert |
| 7,118,553 B2 | 10/2006 | Scherer |
| 7,156,823 B2 | 1/2007 | Landau et al. |
| 7,160,913 B2 | 1/2007 | Schneider |
| 7,294,122 B2 | 11/2007 | Kubo et al. |
| 7,354,427 B2 | 4/2008 | Fangrow |
| RE40,428 E | 7/2008 | Keane et al. |
| 7,442,185 B2 | 10/2008 | Amark et al. |
| 7,470,258 B2 | 12/2008 | Barker et al. |
| 7,507,227 B2 | 3/2009 | Fangrow |
| 7,510,547 B2 | 3/2009 | Fangrow |
| 7,510,548 B2 | 3/2009 | Fangrow |
| 7,513,895 B2 | 4/2009 | Fangrow |
| 7,534,238 B2 | 5/2009 | Fangrow |
| 7,547,300 B2 | 6/2009 | Fangrow |
| 7,569,043 B2 | 8/2009 | Fangrow |
| 7,618,396 B2 | 11/2009 | Slate et al. |
| 7,635,356 B2 | 12/2009 | Stamp |
| 7,645,271 B2 | 1/2010 | Fangrow |
| 7,654,995 B2 | 2/2010 | Warren et al. |
| 7,658,733 B2 | 2/2010 | Fangrow |
| 7,678,333 B2 | 3/2010 | Reynolds et al. |
| 7,682,345 B2 | 3/2010 | Savage |
| 7,717,879 B2 | 5/2010 | Mansouri |
| 7,744,561 B2 * | 6/2010 | Stamp ........................... 604/68 |
| 7,759,654 B2 | 7/2010 | Yan et al. |
| 7,794,434 B2 | 9/2010 | Mounce et al. |
| 7,799,009 B2 | 9/2010 | Niedospial, Jr. et al. |
| 7,811,262 B2 | 10/2010 | Moberg et al. |
| 7,828,764 B2 | 11/2010 | Moberg et al. |
| 7,871,397 B2 | 1/2011 | Schraga |
| 7,879,010 B2 | 2/2011 | Hunn et al. |
| 7,883,499 B2 | 2/2011 | Fangrow |
| 7,959,715 B2 | 6/2011 | Kavazov et al. |
| 7,972,321 B2 | 7/2011 | Fangrow |
| 7,976,499 B2 | 7/2011 | Grunhut et al. |
| 8,100,154 B2 | 1/2012 | Reynolds et al. |
| 8,177,768 B2 | 5/2012 | Leinsing |
| 8,277,414 B2 * | 10/2012 | Barrow-Williams et al. .......................... 604/136 |
| 8,313,463 B2 | 11/2012 | Barrow-Williams et al. |
| 8,409,138 B2 | 4/2013 | James et al. |
| 8,409,141 B2 | 4/2013 | Johansen et al. |
| 8,491,530 B2 | 7/2013 | Maritan |
| 8,696,628 B2 | 4/2014 | Grunhut |
| 8,932,264 B2 | 1/2015 | Desalvo |
| 9,314,574 B2 | 4/2016 | Roberts et al. |
| 2001/0005781 A1 | 6/2001 | Bergens et al. |
| 2001/0021828 A1 | 9/2001 | Fischer et al. |
| 2001/0037087 A1 | 11/2001 | Knauer |
| 2001/0037089 A1 | 11/2001 | Domici, Jr. |
| 2001/0049496 A1 | 12/2001 | Kirchhofer et al. |
| 2001/0051789 A1 | 12/2001 | Parsons |
| 2002/0032412 A1 | 3/2002 | Riemelmoser |
| 2002/0072709 A1 | 6/2002 | Sadowski et al. |
| 2002/0095120 A1 | 7/2002 | Larsen et al. |
| 2002/0151839 A1 | 10/2002 | Landau |
| 2002/0161334 A1 | 10/2002 | Castellano et al. |
| 2002/0165500 A1 | 11/2002 | Bechtold et al. |
| 2002/0173752 A1 | 11/2002 | Polzin |
| 2002/0183690 A1 | 12/2002 | Arnisolle |

(56) References Cited

U.S. PATENT DOCUMENTS

| | | |
|---|---|---|
| 2003/0036679 A1 | 2/2003 | Kortenbach |
| 2003/0036725 A1 | 2/2003 | Lavi et al. |
| 2003/0050609 A1 | 3/2003 | Sams |
| 2003/0060773 A1 | 3/2003 | Nguyen |
| 2003/0065286 A1 | 4/2003 | Landau |
| 2003/0078546 A1 | 4/2003 | Jensen |
| 2003/0088207 A1 | 5/2003 | Rogatchev et al. |
| 2003/0088216 A1 | 5/2003 | Py |
| 2003/0093030 A1 | 5/2003 | Landau |
| 2003/0093035 A1 | 5/2003 | Mohammed |
| 2003/0093036 A1 | 5/2003 | Crossman et al. |
| 2003/0105430 A1 | 6/2003 | Lavi et al. |
| 2003/0109833 A1 | 6/2003 | Sharpe |
| 2003/0120212 A1 | 6/2003 | Dedig et al. |
| 2003/0120222 A1 | 6/2003 | Vaillancourt |
| 2003/0121815 A1 | 7/2003 | Bergeron et al. |
| 2003/0135157 A1 | 7/2003 | Saulenas et al. |
| 2003/0181859 A1 | 9/2003 | Brunel |
| 2003/0184973 A1 | 10/2003 | Nagata et al. |
| 2003/0196928 A1 | 10/2003 | Parsons |
| 2003/0199814 A1 | 10/2003 | Parsons et al. |
| 2003/0208164 A1 | 11/2003 | Botich et al. |
| 2003/0212362 A1 | 11/2003 | Roser |
| 2003/0212370 A1 | 11/2003 | Barrelle |
| 2003/0212380 A1 | 11/2003 | Barrelle |
| 2003/0225368 A1 | 12/2003 | Landau et al. |
| 2003/0229308 A1 | 12/2003 | Tsals et al. |
| 2003/0233070 A1 | 12/2003 | De La Serna et al. |
| 2003/0236502 A1 | 12/2003 | De La Serna et al. |
| 2003/0236504 A1 | 12/2003 | Chen |
| 2004/0002684 A1 | 1/2004 | Lopez |
| 2004/0015134 A1 | 1/2004 | Lavi et al. |
| 2004/0019326 A1 | 1/2004 | Gilbert et al. |
| 2004/0024367 A1* | 2/2004 | Gilbert ............ 604/198 |
| 2004/0039336 A1 | 2/2004 | Amark et al. |
| 2004/0039366 A1 | 2/2004 | MacLeod |
| 2004/0069044 A1 | 4/2004 | Lavi et al. |
| 2004/0087897 A1 | 5/2004 | Hjertman |
| 2004/0094396 A1 | 5/2004 | Lee et al. |
| 2004/0102740 A1 | 5/2004 | Meloul |
| 2004/0111054 A1 | 6/2004 | Landau et al. |
| 2004/0111057 A1 | 6/2004 | Wilkinson |
| 2004/0133159 A1 | 7/2004 | Haider et al. |
| 2004/0138618 A1 | 7/2004 | Mazzoni |
| 2004/0143224 A1 | 7/2004 | Field et al. |
| 2004/0153033 A1 | 8/2004 | Mazzoni |
| 2004/0225262 A1 | 11/2004 | Fathallah et al. |
| 2004/0243065 A1 | 12/2004 | McConnell et al. |
| 2005/0011780 A1 | 1/2005 | Simon et al. |
| 2005/0020979 A1 | 1/2005 | Westbye et al. |
| 2005/0020980 A1 | 1/2005 | Inoue et al. |
| 2005/0027255 A1 | 2/2005 | Lavi et al. |
| 2005/0033234 A1 | 2/2005 | Sadowski et al. |
| 2005/0035029 A1 | 2/2005 | Grob |
| 2005/0040716 A1 | 2/2005 | Schmid et al. |
| 2005/0049550 A1 | 3/2005 | Kirchhofer et al. |
| 2005/0049561 A1 | 3/2005 | Hommann et al. |
| 2005/0075608 A1 | 4/2005 | Holdgate et al. |
| 2005/0085776 A1 | 4/2005 | Hommann et al. |
| 2005/0090782 A1 | 4/2005 | Marshall et al. |
| 2005/0097238 A1 | 5/2005 | Oomori et al. |
| 2005/0101919 A1 | 5/2005 | Brunnberg |
| 2005/0113747 A1 | 5/2005 | Moir |
| 2005/0124940 A1 | 6/2005 | Martin et al. |
| 2005/0125019 A1 | 6/2005 | Kudrna et al. |
| 2005/0137523 A1 | 6/2005 | Wyatt et al. |
| 2005/0168855 A1 | 8/2005 | Fanelli et al. |
| 2005/0203466 A1 | 9/2005 | Hommann et al. |
| 2005/0209554 A1 | 9/2005 | Landau |
| 2005/0215941 A1 | 9/2005 | Bernard et al. |
| 2005/0215951 A1 | 9/2005 | Saulenas et al. |
| 2005/0222539 A1 | 10/2005 | Gonzales et al. |
| 2005/0261633 A1 | 11/2005 | Khalaj |
| 2005/0261634 A1 | 11/2005 | Karlsson |
| 2005/0267403 A1 | 12/2005 | Landau et al. |
| 2005/0273054 A1 | 12/2005 | Asch |
| 2005/0273055 A1 | 12/2005 | Harrison et al. |
| 2005/0277885 A1 | 12/2005 | Scherer |
| 2005/0277886 A1 | 12/2005 | Hommann et al. |
| 2005/0277896 A1 | 12/2005 | Messerli et al. |
| 2005/0288633 A1 | 12/2005 | Jeffrey |
| 2006/0016835 A1 | 1/2006 | Perry |
| 2006/0030819 A1 | 2/2006 | Young et al. |
| 2006/0036216 A1 | 2/2006 | Rimlinger et al. |
| 2006/0036217 A1 | 2/2006 | Doyle |
| 2006/0069345 A1 | 3/2006 | Anderson et al. |
| 2006/0069348 A1 | 3/2006 | Parker et al. |
| 2006/0069350 A1 | 3/2006 | Buenger et al. |
| 2006/0079834 A1 | 4/2006 | Tennican et al. |
| 2006/0100588 A1 | 5/2006 | Brunnberg et al. |
| 2006/0106295 A1 | 5/2006 | Jais et al. |
| 2006/0161111 A1 | 7/2006 | Potter et al. |
| 2006/0178630 A1 | 8/2006 | Bostrom et al. |
| 2006/0178631 A1 | 8/2006 | Gillespie et al. |
| 2006/0178642 A1 | 8/2006 | Gillespie et al. |
| 2006/0184119 A1 | 8/2006 | Remde et al. |
| 2006/0184137 A1 | 8/2006 | Reynolds |
| 2006/0189938 A1 | 8/2006 | Hommann et al. |
| 2006/0200093 A1 | 9/2006 | Lopez |
| 2006/0206060 A1 | 9/2006 | Lopez |
| 2006/0224124 A1 | 10/2006 | Scherer |
| 2006/0229572 A1 | 10/2006 | Lopez |
| 2006/0258986 A1 | 11/2006 | Hunter et al. |
| 2006/0258990 A1 | 11/2006 | Weber |
| 2006/0270986 A1 | 11/2006 | Hommann et al. |
| 2007/0027430 A1 | 2/2007 | Hommann |
| 2007/0066939 A1 | 3/2007 | Krulevitch et al. |
| 2007/0078382 A1 | 4/2007 | Hommann et al. |
| 2007/0118094 A1 | 5/2007 | Bingham et al. |
| 2007/0142787 A1 | 6/2007 | Scherer |
| 2007/0156091 A1 | 7/2007 | Fathallah et al. |
| 2007/0156112 A1 | 7/2007 | Walsh |
| 2007/0208296 A1 | 9/2007 | Paproski et al. |
| 2008/0033395 A1 | 2/2008 | Alchas |
| 2008/0172024 A1 | 7/2008 | Yow |
| 2008/0213590 A1 | 9/2008 | Greiner et al. |
| 2008/0269680 A1 | 10/2008 | Ibranyan et al. |
| 2008/0306443 A1 | 12/2008 | Neer et al. |
| 2008/0312602 A1 | 12/2008 | Barrow-Williams et al. |
| 2008/0312606 A1 | 12/2008 | Harrison et al. |
| 2009/0036764 A1 | 2/2009 | Rivas et al. |
| 2009/0054849 A1 | 2/2009 | Burnell et al. |
| 2009/0088688 A1 | 4/2009 | Timothy Donald et al. |
| 2009/0209554 A1 | 8/2009 | Boyd et al. |
| 2009/0234297 A1 | 9/2009 | Jennings |
| 2010/0016793 A1 | 1/2010 | Jennings et al. |
| 2010/0036319 A1 | 2/2010 | Drake et al. |
| 2010/0063444 A1 | 3/2010 | Wikner |
| 2011/0092954 A1 | 4/2011 | Jennings |
| 2011/0098647 A1 | 4/2011 | Jennings |
| 2011/0098655 A1 | 4/2011 | Jennings et al. |
| 2011/0130743 A1 | 6/2011 | Jennings et al. |
| 2011/0282278 A1 | 11/2011 | Stamp et al. |
| 2012/0232491 A1 | 9/2012 | Jennings |
| 2012/0323177 A1 | 12/2012 | Adams et al. |
| 2013/0096512 A1 | 4/2013 | Ekman et al. |
| 2013/0267898 A1 | 10/2013 | Hourmand et al. |
| 2013/0317446 A1 | 11/2013 | Hourmand et al. |
| 2013/0331794 A1 | 12/2013 | Ekman et al. |
| 2013/0338601 A1 | 12/2013 | Cowe |
| 2013/0345643 A1 | 12/2013 | Hourmand et al. |
| 2014/0257193 A1 | 9/2014 | Bostrom et al. |

FOREIGN PATENT DOCUMENTS

| | | |
|---|---|---|
| CN | 2059579 U | 7/1990 |
| CN | 1190599 A | 8/1998 |
| CN | 1420794 A | 5/2003 |
| CN | 1541121 A | 10/2004 |
| CN | 1550240 A | 12/2004 |
| CN | 101014379 A | 8/2007 |
| CN | 101068585 A | 11/2007 |
| DE | 902776 C | 1/1954 |
| DE | 3604826 A1 | 10/1986 |

(56) References Cited

FOREIGN PATENT DOCUMENTS

| | | |
|---|---|---|
| DE | 4428467 A1 | 2/1996 |
| DE | 29513214 U1 | 1/1997 |
| DE | 19603707 A1 | 8/1997 |
| DE | 69506521 T2 | 6/1999 |
| DE | 10137962 A1 | 2/2003 |
| DE | 10207276 A1 | 9/2003 |
| DE | 20311996 U1 | 10/2003 |
| EP | 0111724 B1 | 11/1983 |
| EP | 0096314 A2 | 12/1983 |
| EP | 0144625 A2 | 6/1985 |
| EP | 0240787 A2 | 3/1987 |
| EP | 0338806 A2 | 10/1989 |
| EP | 0515473 B1 | 12/1992 |
| EP | 0518416 A1 | 12/1992 |
| EP | 0331452 A2 | 8/1993 |
| EP | 0585626 A1 | 3/1994 |
| EP | 0389938 B1 | 5/1994 |
| EP | 0516473 B1 | 2/1996 |
| EP | 0482677 B1 | 4/1998 |
| EP | 0602883 B1 | 7/1998 |
| EP | 0857491 A1 | 8/1998 |
| EP | 0824922 B1 | 4/2002 |
| EP | 1260241 A1 | 11/2002 |
| EP | 0824923 B1 | 7/2003 |
| EP | 1228777 B1 | 10/2003 |
| EP | 0991441 B1 | 12/2003 |
| EP | 1166809 B1 | 3/2004 |
| EP | 0666084 B1 | 4/2004 |
| EP | 0941133 B1 | 4/2004 |
| EP | 1124601 B1 | 12/2004 |
| EP | 1364667 B1 | 4/2005 |
| EP | 1208858 B1 | 6/2006 |
| EP | 1755710 A1 | 2/2007 |
| EP | 1586341 B1 | 1/2008 |
| EP | 2023980 A1 | 2/2009 |
| EP | 2129414 A1 | 12/2009 |
| EP | 1755706 B1 | 3/2010 |
| EP | 1928523 B1 | 7/2010 |
| EP | 1518575 B1 | 11/2010 |
| EP | 1932558 B1 | 6/2011 |
| EP | 2468330 A1 | 6/2012 |
| EP | 2340863 B1 | 11/2013 |
| EP | 2620174 B1 | 5/2014 |
| EP | 2675509 B1 | 4/2015 |
| EP | 2705861 B1 | 4/2015 |
| EP | 2414003 B1 | 5/2015 |
| EP | 2464401 B1 | 5/2015 |
| EP | 2493531 B1 | 7/2015 |
| EP | 2705862 B1 | 7/2015 |
| EP | 2588173 B1 | 10/2015 |
| EP | 2470241 B1 | 11/2015 |
| EP | 2768556 B1 | 12/2015 |
| EP | 2355872 B1 | 1/2016 |
| EP | 2720738 B1 | 1/2016 |
| EP | 1412000 B1 | 2/2016 |
| EP | 2671606 B1 | 3/2016 |
| EP | 2760507 B1 | 4/2016 |
| FR | 1014881 A | 8/1952 |
| FR | 1169935 A | 1/1959 |
| FR | 1538565 A | 9/1968 |
| FR | 2506161 A1 | 11/1982 |
| FR | 2629706 A | 10/1989 |
| FR | 2654938 A1 | 5/1991 |
| FR | 2665079 A1 | 1/1992 |
| FR | 2717086 A1 | 9/1995 |
| FR | 2741810 A1 | 6/1997 |
| FR | 2805868 A1 | 9/2001 |
| FR | 2830765 A1 | 4/2003 |
| FR | 2861310 A1 | 4/2005 |
| GB | 143084 | 5/1920 |
| GB | 0412054 | 6/1934 |
| GB | 728248 | 4/1955 |
| GB | 909898 | 11/1962 |
| GB | 1263355 | 2/1972 |
| GB | 1311937 A | 3/1973 |
| GB | 1514725 A | 6/1978 |
| GB | 2338033 A | 12/1999 |
| GB | 2388033 A | 11/2003 |
| GB | 2396298 A | 6/2004 |
| GB | 2396816 A | 7/2004 |
| GB | 2397767 A | 8/2004 |
| GB | 2404338 A | 2/2005 |
| GB | 2414398 A | 11/2005 |
| GB | 2414399 A | 11/2005 |
| GB | 2414400 A | 11/2005 |
| GB | 2414401 A | 11/2005 |
| GB | 2414402 A | 11/2005 |
| GB | 2414403 A | 11/2005 |
| GB | 2424835 A | 10/2006 |
| GB | 2424836 A | 10/2006 |
| GB | 2424837 A | 10/2006 |
| GB | 2424838 A | 10/2006 |
| GB | 2425062 A | 10/2006 |
| GB | 2433035 A | 6/2007 |
| GB | 2437922 A | 11/2007 |
| GB | 2438591 A | 12/2007 |
| GB | 2443606 A | 5/2008 |
| GB | 2445090 A | 6/2008 |
| GB | 2446778 A | 8/2008 |
| GB | 2451663 A | 2/2009 |
| GB | 2451665 A | 2/2009 |
| GB | 2452286 A | 3/2009 |
| GB | 2515041 B | 12/2014 |
| JP | 59-115053 A | 7/1984 |
| JP | 2-185261 A | 7/1990 |
| JP | 2-502971 T | 9/1990 |
| JP | H02-299660 A | 12/1990 |
| JP | 11-501549 T | 2/1992 |
| JP | 5-161712 A | 6/1993 |
| JP | 6-209996 A | 8/1994 |
| JP | 6-508773 T | 10/1994 |
| JP | 6-327770 A | 11/1994 |
| JP | H07-116224 A | 5/1995 |
| JP | 7-213610 A | 8/1995 |
| JP | 7-222799 A | 8/1995 |
| JP | 8-502180 T | 3/1996 |
| JP | 8-504354 T | 5/1996 |
| JP | 9-225029 A | 9/1997 |
| JP | 10-504474 T | 5/1998 |
| JP | 10-507935 T | 8/1998 |
| JP | 11-503637 T | 3/1999 |
| JP | 11-504536 T | 4/1999 |
| JP | 11-164887 T | 6/1999 |
| JP | 11-512332 T | 10/1999 |
| JP | 2000-126293 A | 5/2000 |
| JP | 2000-510021 T | 8/2000 |
| JP | 2001-046498 A | 2/2001 |
| JP | 2001-212237 A | 8/2001 |
| JP | 2002-500933 T | 1/2002 |
| JP | 2002-502296 A | 1/2002 |
| JP | 2002-095749 A | 4/2002 |
| JP | 2002-513547 T | 5/2002 |
| JP | 2002-526175 A | 8/2002 |
| JP | 2002-528182 T | 9/2002 |
| JP | 2002-532161 T | 10/2002 |
| JP | 2003-511105 T | 3/2003 |
| JP | 2003-532500 T | 11/2003 |
| JP | 2003-533288 A | 11/2003 |
| JP | 2004-533282 T | 11/2004 |
| JP | 2004-537376 A | 12/2004 |
| JP | 2005-508214 A | 3/2005 |
| JP | 2005-177503 A | 7/2005 |
| JP | 2004-33737 A | 8/2005 |
| JP | 2006-223858 A | 8/2006 |
| JP | 2007-207611 A | 8/2007 |
| JP | 2008-284177 A | 11/2008 |
| NZ | 335985 A | 4/2001 |
| NZ | 573171 A | 11/2010 |
| NZ | 573350 A | 12/2010 |
| WO | WO 87/07843 A1 | 12/1987 |
| WO | WO 88/08725 | 11/1988 |
| WO | WO 88/10129 A1 | 12/1988 |
| WO | WO 92/19296 A | 11/1992 |
| WO | WO 93/02186 A1 | 2/1993 |

(56) References Cited

FOREIGN PATENT DOCUMENTS

| | | |
|---|---|---|
| WO | WO 93/21986 A2 | 11/1993 |
| WO | WO 93/23098 A1 | 11/1993 |
| WO | WO 94/04207 A1 | 3/1994 |
| WO | WO 94/07554 A1 | 4/1994 |
| WO | WO 94/11041 | 5/1994 |
| WO | WO 94/13342 A1 | 6/1994 |
| WO | WO 94/21316 A1 | 9/1994 |
| WO | WO 94/22511 A1 | 10/1994 |
| WO | WO 95/04562 A1 | 2/1995 |
| WO | WO 95/29720 A1 | 11/1995 |
| WO | WO 95/31235 A1 | 11/1995 |
| WO | WO 95/35126 A1 | 11/1995 |
| WO | WO 95/35126 A1 | 12/1995 |
| WO | WO 96/30065 A1 | 10/1996 |
| WO | WO 97/10865 A1 | 3/1997 |
| WO | WO 97/13538 A1 | 4/1997 |
| WO | WO 97/48430 A1 | 12/1997 |
| WO | WO 98/11927 A1 | 3/1998 |
| WO | WO 99/03529 A2 | 1/1999 |
| WO | WO 99/10030 A2 | 3/1999 |
| WO | WO 99/22789 A1 | 5/1999 |
| WO | WO 9922789 * | 5/1999 |
| WO | WO 99/37343 A | 7/1999 |
| WO | WO 99/53979 A1 | 10/1999 |
| WO | WO 99/59658 A1 | 11/1999 |
| WO | WO 00/06227 A1 | 2/2000 |
| WO | WO 00/07539 A1 | 2/2000 |
| WO | WO 00/13723 A2 | 3/2000 |
| WO | WO 00/24441 A1 | 5/2000 |
| WO | WO 00/35516 | 6/2000 |
| WO | WO 00/50107 A1 | 8/2000 |
| WO | WO 00/61209 A1 | 10/2000 |
| WO | WO 00/64515 A1 | 11/2000 |
| WO | WO 00/69488 A2 | 11/2000 |
| WO | WO 01/05456 A1 | 1/2001 |
| WO | WO 01/49347 A1 | 7/2001 |
| WO | WO 01/60435 A1 | 8/2001 |
| WO | WO 01/76666 A1 | 10/2001 |
| WO | WO 01/77384 A2 | 10/2001 |
| WO | WO 01/87384 A1 | 11/2001 |
| WO | WO 02/11799 A1 | 2/2002 |
| WO | WO 02/47746 A1 | 6/2002 |
| WO | WO 02/056947 A1 | 7/2002 |
| WO | WO 02/074361 A2 | 9/2002 |
| WO | WO 03/013632 A2 | 2/2003 |
| WO | WO 03/015846 A2 | 2/2003 |
| WO | WO 03/015853 A1 | 2/2003 |
| WO | WO 03/039633 A2 | 5/2003 |
| WO | WO 03/041768 A | 5/2003 |
| WO | WO 03/047663 A2 | 6/2003 |
| WO | WO 03/051434 A2 | 6/2003 |
| WO | WO 03/066141 A1 | 8/2003 |
| WO | WO 03/092771 | 11/2003 |
| WO | WO 03/097133 | 11/2003 |
| WO | WO 03/099358 A2 | 12/2003 |
| WO | WO 2004/007554 A1 | 1/2004 |
| WO | WO 2004/011065 A1 | 2/2004 |
| WO | WO 2004/030732 A2 | 4/2004 |
| WO | WO 2004/035117 A2 | 4/2004 |
| WO | WO 2004/047890 A1 | 6/2004 |
| WO | WO 2004/047891 A1 | 6/2004 |
| WO | WO 2004/047892 A | 6/2004 |
| WO | WO 2004/054644 A1 | 7/2004 |
| WO | WO 2004/054645 A3 | 7/2004 |
| WO | WO 2004/087242 A1 | 10/2004 |
| WO | WO 2004/101025 A2 | 11/2004 |
| WO | WO 2004/108194 A1 | 12/2004 |
| WO | WO 2004108194 * | 12/2004 |
| WO | WO 2005/004961 A1 | 1/2005 |
| WO | WO 2005/009515 A1 | 2/2005 |
| WO | WO 2005/023341 A1 | 3/2005 |
| WO | WO 2005/025636 A2 | 3/2005 |
| WO | WO 2005/030301 A1 | 4/2005 |
| WO | WO 2005/035028 A1 | 4/2005 |
| WO | WO 2005/044345 A | 5/2005 |
| WO | WO 2005/044347 A1 | 5/2005 |
| WO | WO 2005/058393 A2 | 6/2005 |
| WO | WO 2005/058396 A1 | 6/2005 |
| WO | WO 2005/070481 A1 | 8/2005 |
| WO | WO 2005/082438 A1 | 9/2005 |
| WO | WO 2005/097238 A3 | 10/2005 |
| WO | WO 2005/105014 A2 | 11/2005 |
| WO | WO 2005/115507 A1 | 12/2005 |
| WO | WO 2005/115508 A1 | 12/2005 |
| WO | WO 2005/115509 A1 | 12/2005 |
| WO | WO 2005/115510 A1 | 12/2005 |
| WO | WO 2005/115512 A1 | 12/2005 |
| WO | WO 2005/115513 A1 | 12/2005 |
| WO | WO 2005/115514 A1 | 12/2005 |
| WO | WO 2005/115516 A1 | 12/2005 |
| WO | WO 2005/120607 A2 | 12/2005 |
| WO | WO 2006/008086 A1 | 1/2006 |
| WO | WO 2006/044236 A2 | 4/2006 |
| WO | WO 2006/050304 A1 | 5/2006 |
| WO | WO 2006/062788 A2 | 6/2006 |
| WO | WO 2006/063015 A2 | 6/2006 |
| WO | WO 2006/063124 A2 | 6/2006 |
| WO | WO 2006/088513 A1 | 8/2006 |
| WO | WO 2006/088630 A2 | 8/2006 |
| WO | WO 2006/099441 A2 | 9/2006 |
| WO | WO 2006/106290 A1 | 10/2006 |
| WO | WO 2006/106291 A1 | 10/2006 |
| WO | WO 2006/106292 A1 | 10/2006 |
| WO | WO 2006/106293 A1 | 10/2006 |
| WO | WO 2006/106294 A | 10/2006 |
| WO | WO 2006/106295 A1 | 10/2006 |
| WO | WO 2006/118616 A1 | 11/2006 |
| WO | WO 2006/129196 A1 | 12/2006 |
| WO | WO 2007/027204 A2 | 3/2007 |
| WO | WO 2007/036676 A1 | 4/2007 |
| WO | WO 2007/047200 A1 | 4/2007 |
| WO | WO 2007/051330 A1 | 5/2007 |
| WO | WO 2007/066152 A | 6/2007 |
| WO | WO 2007/066152 A2 | 6/2007 |
| WO | WO 2007/122193 A1 | 11/2007 |
| WO | WO 2007/129324 A2 | 11/2007 |
| WO | WO 2007/131013 A | 11/2007 |
| WO | WO 2007/138299 A1 | 12/2007 |
| WO | WO 2008/047372 A2 | 4/2008 |
| WO | WO 2008/075033 A | 6/2008 |
| WO | WO 2008/093063 A2 | 8/2008 |
| WO | WO 2010/023303 A1 | 3/2010 |
| WO | WO 2012/000835 A1 | 1/2012 |

OTHER PUBLICATIONS

International Search Report dated Sep. 5, 2005; International Application No. PCT/GB2005/002117.
International Search Report dated May 30, 2006; International Application No. PCT/GB2005/003725.
International Search Report dated Sep. 9, 2005; International Application No. PCT/GB2005/002126.
Australian Search Report dated Dec. 6, 2007; Application No. SG 200608164-0.
International Search Report dated Sep. 5, 2005; International Application No. PCT/GB2005/002131.
Austrian Search Report dated Jan. 22, 2006; Application No. 200608166-5.
International Search Report dated Sep. 9, 2005; International Application No. PCT/GB2005/002120.
International Search Report dated Sep. 6, 2005; International Application No. PCT/GB2005/002108.
European Search Report dated Apr. 23, 2007; Application No. 06077332.2.
International Search Report dated Sep. 5, 2005; International Application No. PCT/GB2005/002105.
Singapore Search Report dated Feb. 26, 2008; Application No. 200608070-9.
International Search Report dated Sep. 5, 2005; International Application No. PCT/GB2005/002116.
International Search Report dated Sep. 5, 2005; International Application No. PCT/GB2005/002128.

(56) References Cited

OTHER PUBLICATIONS

Australian Search Report dated Dec. 11, 2007; Application No. 200608165-7.
International Search Report dated May 23, 2006; International Application No. PCT/GB2006/001017.
International Search Report dated May 29, 2006; International Application No. PCT/GB2006/001018.
International Search Report dated Jun. 2, 2006; International Application No. PCT/GB2006/001030.
International Search Report dated Jun. 1, 2006; International Application No. PCT/GB2006/001029.
International Search Report dated Sep. 9, 2005 International Application No. PCT/GB2005/002135.
International Search Report dated May 30, 2006; International Application No. PCT/GB2006/001031.
International Search Report dated Jun. 27, 2006; International Application No. PCT/GB2006/001023.
International Search Report dated Feb. 27, 2007; International Application No. PCT/1B2006/002792.
European Search Report dated Feb. 1, 2006; Application No. 05255298.1.
Great Britain Search Report dated Sep. 22, 2006; Application No. GB0610860.9.
International Search Report dated Aug. 22, 2007; International Application No. PCT/GB2007/001992.
International Search Report dated Sep. 4, 2007; International Application No. PCT/GB2007/002002.
Great Britain Search Report dated Sep. 28, 2006; Application No. GB0610859.1.
International Search Report dated Aug. 22, 2007; International Application No. PCT/GB2007/001973.
International Search Report dated Feb. 26, 2008; International Application No. PCT/GB2007/004335.
International Search Report dated Sep. 13, 2007; International Application No. PCT/GB2007/001999.
International Search Report dated Aug. 28, 2007; International Application No. PCT/GB2007/001969.
International Search Report dated Oct. 10, 2008; International Application No. PCT/GB2008/002578.
Great Britain Search Report dated Nov. 12, 2007; Application No. GB0715460.2.
International Search Report dated Oct. 14, 2008; International Application No. PCT/GB2008/002580.
Great Britain Search Report dated Nov. 12, 2007; Application No. GB0715459.4.
International Search Report dated Nov. 27, 2008; International Application No. PCT/GB2008/002579.
Great Britain Search Report dated Nov. 12, 2007; Application No. GB0715461.0.
International Search Report dated Oct. 10, 2008; International Application No. PCT/GB2008/002573.
Great Britain Search Report dated Nov. 12, 2007; Application No. GB0715456.0.
International Search Report dated Oct. 10, 2008; International Application No. PCT/GB2008/002583.
Great Britain Search Report dated Nov. 12, 2007; Application No. GB0715457.8.
International Search Report dated Sep. 30, 2009; International Application No. PCT/GB2009/001447.
Great Britain Search Report dated Sep. 25, 2008; Application No. GB0811348.2.
International Search Report dated Oct. 2, 2009; International Application No. PCT/GB2009/001448.
Great Britain Search Report dated Sep. 25, 2008; Application No. GB0811346.6.
International Search Report dated Oct. 5, 2009; International Application No. PCT/GB2009/001451.
Great Britain Search Report dated Sep. 25, 2008; Application No. GB0811347.4.
International Search Report dated Oct. 6, 2009; International Application No. PCT/GB2009/001453.
Great Britain Search Report dated Sep. 25, 2008; Application No. GB0811345.8.
International Search Report dated Oct. 5, 2009; International Application No. PCT/GB2009/001445.
Great Britain Search Report dated Sep. 25, 2008; Application No. GB0811349.0.
International Search Report dated Jan. 22, 2010; International Application No. PCT/GB2009/001446.
Great Britain Search Report dated Sep. 25, 2008; Application No. GB0811343.3.
International Search Report dated Jan. 12, 2008; International Application No. PCT/GB2008/002475.
Great Britain Search Report dated Nov. 16, 2007; Application No. GB0716774.5.
European Search Report dated Aug. 3, 2011; Application No. 11163779.9.
Singapore Search Report dated Mar. 15, 2012; Application No. SG 201007017-5.
European Search Report dated Jul. 20, 2011; Application No. 11163762.5.
Australian Search Report dated Feb. 26, 2008; Application No. SG 200608071-7.
International Search Report dated Sep. 5, 2005; International Application No. PCT/GB2005/002137.
European Search Report dated Feb. 28, 2011; Application No. 10179733.0.
European Search Report dated Mar. 4, 2011; Application No. 10179736.3.
European Search Report dated Jun. 16, 2011; Application No. 11160134.0.
European Search Report dated Apr. 17, 2012; International Application No. 12157660.7.
European Search Report dated Apr. 17, 2012; International Application No. 12157661.5.
European Search Report Dated Oct. 16, 2012; International Application No. 12177505.0.
European Search Report dated Aug., 4, 2011; Application No. 11169691.0.
Great Britain Search Report dated Sep. 29, 2006; Application No. GB0610856.7.
Great Britain Search Report dated Sep. 19, 2006; Application No. GB0610861.7.
European Search Report dated Oct. 15, 2013; Application No. 12182553.3.
Great Britain Search Report dated Dec. 9, 2013; Application No. GB1310394.0.
International Search Report dated Sep. 8, 2014; International Application No. PCT/EP2014/062163.
Great Britain Search Report dated Dec. 8, 2013; Application No. GB1310389.0.
International Search Report dated Sep. 8, 2014; International Application No. PCT/EP2014/062166.
Great Britain Search Report dated Dec. 9, 2013; Application No. GB1310402.1.
International Search Report dated Sep. 17, 2014; International Application No. PCT/EP2014/062167.
Great Britain Search Report dated Dec. 9, 2013; Application No. GB1310392.4.
International Search Report dated Sep. 9, 2014; International Application No. PCT/EP2014/062168.
Great Britain Search Report dated Dec. 10, 2013; Application No. GB1310393.2.
International Search Report dated Sep. 8, 2014; International Application No. PCT/EP2014/062162.
Great Britain Search Report dated Dec. 10, 2013; Application No. GB1310372.6.
International Search Report dated Sep. 16, 2014; International Application No. PCT/EP2014/062160.
International Search Report dated Jan. 29, 2015; International Application No. PCT/EP2014/062167.

(56) References Cited

OTHER PUBLICATIONS

European Search Report dated Apr. 28, 2015; Application No. 15153304.9.
International Preliminary Report dated Dec. 15, 2015; International Application No. PCT/EP2014/062163.
International Preliminary Report dated Dec. 15, 2015; International Application No. PCT/EP2014/062166.

* cited by examiner

INJECTION DEVICE

BACKGROUND TECHNOLOGY

The present invention relates to a releasable coupling for use in an injection device of the type that receives a syringe, extends it, discharges its contents and then retracts it automatically. Devices of this general description are shown in WO 95/35126 and EP-A-0 516 473 and tend to employ a drive spring and some form of release mechanism that releases the syringe from the influence of the drive spring once its contents are supposed to have been discharged, to allow it to be retracted by a return spring.

Because of the stack-up of tolerances of the various components of the device, a certain margin of safety must be built into the activation of the release mechanism, to ensure that it is effective. The consequence of underestimating the safety margin is that the release mechanism may fail to operate even once the syringe contents have been discharged, which is unsatisfactory in a device that is supposed to retract automatically, particularly for self-administered drugs. On the other hand, overestimating the safety margin may mean that some of the syringe contents are discharged after the syringe has retracted, which results firstly in a short dose and secondly in what may be termed a "wet" injection. Wet injections are undesirable for the squeamish, particularly in connection with self-administered drugs.

UK patent publication nos. 2388033, 2396298 and 2397767 describe a series of injection devices designed to deal with this problem. Each makes use of a neat trick that delays the release of the syringe for a certain period of time after the release mechanism has been activated, in an attempt to ensure that the syringe has been completely discharged. The devices illustrated in UK patent application no. 0325596 make use of a two-part drive incorporating a fluid-damped delay mechanism that is particularly effective in ensuring complete discharge of the syringe contents. In each case, the device relies upon two unlatching mechanisms. The first unlatching mechanism initiates the fluid damping mechanism and the second releases the syringe from the actuator, allowing it to be withdrawn. The unlatching mechanisms are activated by components of the injection device having been advanced to nominal unlatching positions relative to the device casework. Unlatching mechanisms, including the mechanisms described in the present application, that are activated by components of the injection device having been advanced to nominal unlatching positions relative to the syringe are described in our concurrently filed UK application with publication no. 2414399.

Figure 1:
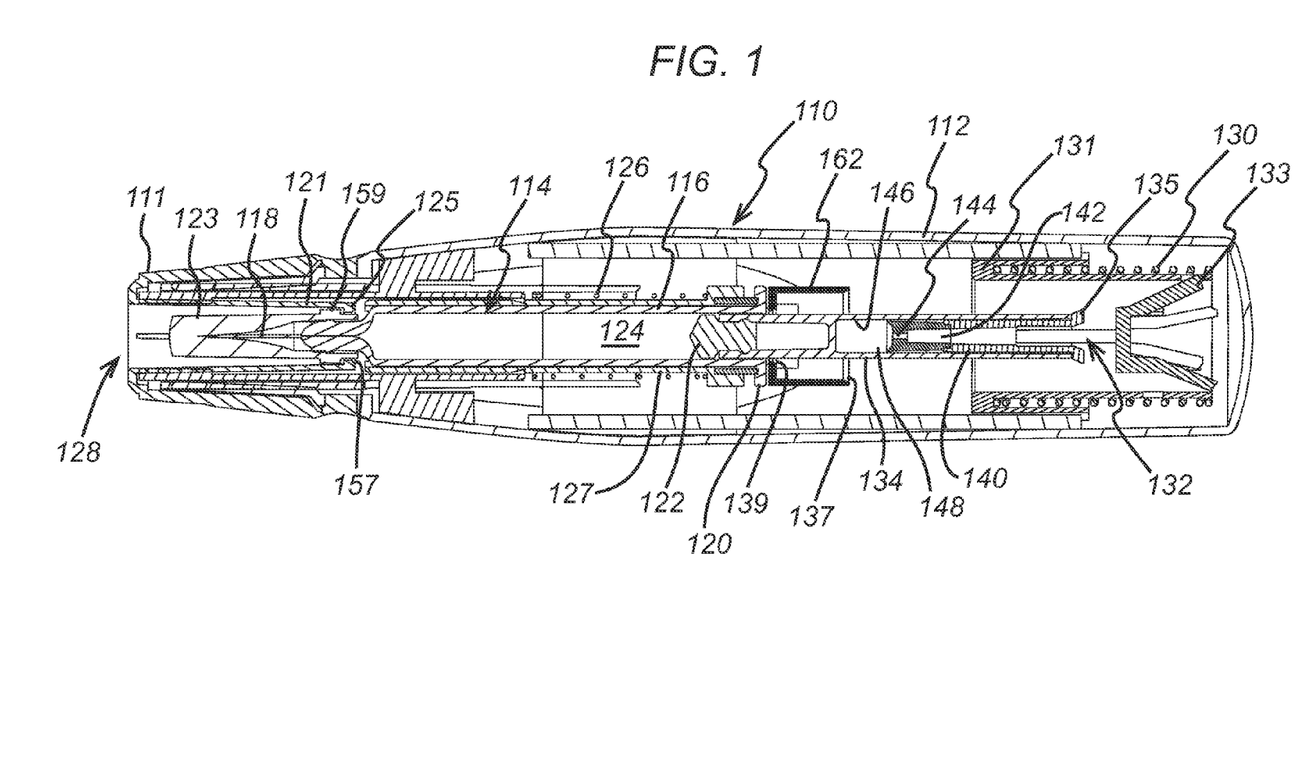
FIG. 1 is an illustration of a comparative injection device as discussed above.

FIG. 1 shows just such an injection device 110 in which a housing 112 contains a hypodermic syringe 114. The syringe 114 is of conventional type, including a syringe body 116 terminating at one end in a hypodermic needle 118 and at the other in a flange 120. The conventional plunger that would normally be used to discharge the contents of the syringe 114 manually have been removed and replaced with a drive element 134 as will be described below, terminating in a bung 122. This drive element 134 constrains a drug 124 to be administered within the syringe body 116. Whilst the syringe illustrated is of hypodermic type, this need not necessarily be so. Transcutaneous or ballistic dermal and subcutaneous syringes may also be used with the injection device of the present invention. Generally, the syringe must include a discharge nozzle, which in a hypodermic syringe is the needle 118.

As illustrated, the housing includes a return spring 126 that biases the syringe 114 from an extended position in which the needle 118 extends from an aperture 128 in the housing 112 to a retracted position in which the discharge nozzle 118 is contained within the housing 112. The return spring 126 acts on the syringe 114 via a sleeve 127.

At the other end of the housing is a compression drive spring 130. Drive from the drive spring 130 is transmitted via a multi-component drive to the syringe 114 to advance it from its retracted position to its extended position and discharge its contents through the needle 118. The drive accomplishes this task by acting directly on the drug 124 and the syringe 114. Hydrostatic forces acting through the drug and, to a lesser extent, static friction between the bung 122 and the syringe body 116 initially ensures that they advance together, until the return spring 126 bottoms out or the syringe body 116 meets some other obstruction that retards its motion.

The multi-component drive between the drive spring 130 and the syringe 114 consists of three principal components. A drive sleeve 131 takes drive from the drive spring 130 and transmits it to flexible latch arms 133 on a first drive element 132. This in turn transmits drive via flexible latch arms 135 to a second drive element, the drive element 134 already mentioned.

The first drive element 132 includes a hollow stem 140, the inner cavity of which forms a collection chamber 142 in communication with a vent 144 that extends from the collection chamber through the end of the stem 140. The second drive element 134 includes a blind bore 146 that is open at one end to receive the stem 140 and closed at the other. As can be seen, the bore 146 and the stem 140 define a fluid reservoir 148, within which a damping fluid is contained.

A trigger (not shown) is provided at the middle of the housing 112 and, when operated, serves to decouple the drive sleeve 131 from the housing 112, allowing it to move relative to the housing 112 under the influence of the drive spring 130. The operation of the device is then as follows.

Initially, the drive spring 130 moves the drive sleeve 131, the drive sleeve 131 moves the first drive element 132 and the first drive element 132 moves the second drive element 134, in each case by acting through the flexible latch arms 133, 135. The second drive element 134 moves and, by virtue of static friction and hydrostatic forces acting through the drug 124 to be administered, moves the syringe body 116 against the action of the return spring 126. The return spring 126 compresses and the hypodermic needle 118 emerges from the exit aperture 128 of the housing 112. This continues until the return spring 126 bottoms out or the syringe body 116 meets some other obstruction that retards its motion. Because the static friction between the second drive element 134 and the syringe body 116 and the hydrostatic forces acting through the drug 124 to be administered are not sufficient to resist the full drive force developed by the drive spring 130, at this point the second drive element 134 begins to move within the syringe body 116 and the drug 124 begins to be discharged. Dynamic friction between the second drive element 134 and the syringe body 116 and hydrostatic forces acting through the drug 124 to be administered are, however, sufficient to retain the return spring 126 in its compressed state, so the hypodermic needle 118 remains extended.

Before the second drive element 134 reaches the end of its travel within the syringe body 116, so before the contents of the syringe have fully discharged, the flexible latch arms 135 linking the first and second drive elements 132, 134 reach a constriction 137. The constriction 137 is formed by a component 162 that is attached to the syringe flange 120, so it will be understood that when the syringe 114 advances from its retracted position to its extended position, the component 162 advances with it. The constriction 137 moves the flexible latch arms 135 inwards from the position shown to a position at which they no longer couple the first drive element 136 to the second drive element 134, aided by the bevelled surfaces on the constriction 137. Once this happens, the first drive element 136 acts no longer on the second drive element 134, allowing the first drive element 132 to move relative to the second drive element 134.

One drawback associated with this arrangement is that the latch arms 135 are flexed by a constriction 137 through which the drive elements must pass, and which can therefore, at best, flex the latch arms 135 so that their outer extremities coincide with the outer surface of the second drive element 134. As the first and second drive elements 132, to move relative to each other, the latch arms 135 must flex further, so that their outer extremities coincide with the inner surface of the second drive element 134. This requirement introduces manufacturing difficulties and may also affect the reliability of the unlatching mechanism itself.

Because the damping fluid is contained within a reservoir 148 defined between the end of the first drive element 132 and the blind bore 146 in the second drive element 134, the volume of the reservoir 148 will tend to decrease as the first drive element 132 moves relative to the second drive element 134 when the former is acted upon by the drive spring 130. As the reservoir 148 collapses, damping fluid is forced through the vent 144 into the collection chamber 142. Thus, once the flexible latch arms 135 have been released, the force exerted by the drive spring 130 does work on the damping fluid, causing it to flow through the constriction formed by the vent 144, and also acts hydrostatically through the fluid and through friction between the first and second drive elements 132, 134, to drive the second drive element 134. Losses associated with the flow of the damping fluid do not attenuate the force acting on the body of the syringe to a great extent. Thus, the return spring 126 remains compressed and the hypodermic needle 118 remains extended.

After a time, the second drive element 134 completes its travel within the syringe body 116 and can go no further. At this point, the contents of the syringe 114 are completely discharged and the force exerted by the drive spring 130 acts to retain the second drive element 134 in its terminal position and to continue to cause the damping fluid to flow through the vent 144, allowing the first drive element 132 to continue its movement.

Before the reservoir 148 of fluid is exhausted, the flexible latch arms 133 linking the drive sleeve 131 with the first drive element 132 reach another constriction 139, also provided by the component 162 that is attached to the syringe flange 120. The constriction 139 moves the flexible latch arms 133 inwards from the position shown to a position at which they no longer couple the drive sleeve 131 to the first drive element 132, aided by the bevelled surfaces on the constriction 139. Once this happens, the drive sleeve 131 acts no longer on the first drive element 132, allowing them to move relative to each other.

The latch arms 133 must be capable of supporting high shock load at the start of stroke, but must also be capable of releasing with relatively low unlatching forces. Tests have shown that this dual requirement is very difficult to achieve with flexible latch arms 133: if the latch arms are made stiff enough to carry the shock load, they may easily became too stiff to unlatch with acceptably small forces.

Once the drive sleeve 131 is acting no longer on the first drive element 132, of course, the syringe 114 is released, because the force developed by the drive spring 130 is no longer being transmitted to the syringe 114, and the only force acting on the syringe will be the return force from the return spring 126. Thus, the syringe 114 now returns to its retracted position and the injection cycle is complete.

All this takes place only once the cap 111 has been removed from the end of the housing 112 and the boot 123 from the syringe.

SUMMARY OF THE INVENTION

As discussed above, there are two shortcomings in the design illustrated in FIG. 1. The first is that to enable the first and second drive elements to move relative to each other, the latch arms must flex further than they are flexed by the constriction through which they are caused to pass. This requirement introduces manufacturing difficulties and may also affect the reliability of the unlatching mechanism itself. It is an objective of the present invention to provide an improved drive coupling and unlatching mechanism that does not suffer from this shortcoming.

Accordingly, the present invention provides a releasable drive coupling comprising:
  a first drive element having a first projecting flexible arm; and
  a second drive element capable of sliding relative to the first drive element and having:
    a drive surface adapted to receive the first flexible arm, to allow axial loads to be transmitted from one drive element to the other; and
    a second projecting flexible arm so positioned relative to the drive surface that inward flexing of the second flexible arm causes it to act upon the first flexible arm and flex the latter to a point at which it is no longer received by the drive surface, at which point the first and second drive elements are free to slide relative to one another and the drive coupling is thus disengaged.

It will immediately be seen that, owing to the use of the first flexible arms to flex the second flexible arms, there is no longer any need for the second flexible arms to flex further as the drive elements move relative to each other.

Preferably, the first flexible arms operate in compression to transmit axial loads from one drive element to the other. This deals with one problem of using flexible arms under tension, which can be difficult to delatch, needing a relatively high delatching force. An arm in compression provides a good ratio of carrying load to delatching load and is a stable configuration.

For convenience, the coupling may be arranged as follows:
  the first drive element is an inner drive element;
  the first flexible arm projects outwardly from the inner drive element;
  the second drive element is an outer drive element capable of sliding over the inner drive element;
  the second flexible arm projects outwardly from the outer drive element; and
  inward flexing of the outer flexible arm causes it to flex the inner flexible arm inwardly.

Preferably, the outer drive element has a bore in which the inner drive element is received. The inner drive element may have a plurality of outwardly projecting, inner flexible arms and the outer drive element a corresponding plurality of drive surfaces and a corresponding plurality of outwardly projecting, outer flexible arms. For reasons of symmetry, such outwardly projecting, inner and outer flexible arms may be substantially equidistantly spaced around the circumference of the inner drive element.

A simple extension of the present invention provides an automatically releasable drive coupling comprising:
a releasable drive coupling according to the invention;
an actuator acting upon one of the drive components; and
a decoupling component so arranged that, as the outer drive element is advanced by the actuator, it flexes the outer flexible arm inwardly, automatically disengaging the drive coupling.

The decoupling component may comprise a channel through which the inner and outer drive elements pass when acted upon by the actuator, the channel being so arranged that, as the outer drive element passes through it, it flexes the outer flexible arm inwardly, automatically disengaging the drive coupling.

In its application to an injection device, the present invention provides:
a housing adapted to receive a syringe having a discharge nozzle, the housing including means for biasing the syringe from an extended position in which the discharge nozzle extends from the housing to a retracted position in which the discharge nozzle is contained within the housing;
an automatically releasable drive coupling according to the invention in which:
the inner drive element is acted upon by the actuator and the outer drive element acts upon the syringe to advance it from its retracted position to its extended position and discharge its contents through the discharge nozzle; and
the decoupling component automatically disengages the drive coupling when the drive elements have been advanced to a nominal decoupling position.

The second drawback associated with the arrangement of FIG. 1 is that the dual requirement of stiffness and flexibility in the latch arms coupling the actuator to the first drive element is difficult to meet. It is a further objective of the present invention to obviate that requirement. Accordingly, a second aspect of the present invention provides an injection device comprising:
a housing adapted to receive a syringe having a discharge nozzle, the housing including means for biasing the syringe from an extended position in which the discharge nozzle extends from the housing to a retracted position in which the discharge nozzle is contained within the housing;
an actuator;
first and second drive elements, of which the first is acted upon by the actuator and in turn acts upon the second, and the second acts upon the syringe to advance it from its retracted position to its extended position and discharge its contents through the discharge nozzle, the first drive element being capable of movement relative to the second when the first is acted upon by the actuator and the second is restrained by the syringe;
of the actuator and the first drive element, one comprises a flexible arm that engages with a second drive surface on the other, allowing the actuator to act upon the first drive element and preventing the former from moving relative to the latter; and
the second drive element comprises a stop that prevents the flexible arm disengaging from the drive surface until the first drive element has been advanced to a nominal release position relative to the second, whereupon the flexible arm disengages from the second drive surface, allowing the actuator to move relative to the first drive element and thus releasing the syringe from the action of the actuator, whereupon the biasing means restores the syringe to its retracted position.

By the same token, there is also provided an injection device comprising:
a housing adapted to receive a syringe having a discharge nozzle, the housing including means for biasing the syringe from an extended position in which the discharge nozzle extends from the housing to a retracted position in which the discharge nozzle is contained within the housing;
an actuator;
a drive, acted upon by the actuator and acting upon the syringe to discharge its contents through the discharge nozzle; and
of the actuator and the drive, one comprises a flexible arm that engages with a drive surface on the other, allowing the actuator to act upon the drive and preventing the former from moving relative to the latter;
in which the flexible arm is prevented from disengaging from the drive surface until the drive has been advanced to a nominal release position, whereupon the flexible arm disengages from the drive surface, allowing the actuator to move relative to the drive and thus releasing the syringe from the action of the actuator, whereupon the biasing means restores the syringe to its retracted position.

The use of a stop to restrain the flexible arm and prevent its disengagement from the drive surface means that it need not be made as stiff as was the case with FIG. 1. Hence a more flexible material can be used and the shortcomings associated with the arrangement of FIG. 1 are avoided.

Preferably, the action of the actuator on the first drive element tends to disengage the flexible arm from the drive surface, but is prevented from doing so by the stop until the said nominal release position has been reached.

In a convenient implementation of this aspect of the invention, the second flexible arm includes a detent and the stop is in register with the detent when the said nominal release position is reached, thus allowing the flexible arms to flex. Preferably, the second flexible arm is biased toward a position at which it engages the second drive surface and the action of the actuator causes it to move against its bias, thus disengaging it from the drive surface.

BRIEF DESCRIPTION OF THE DRAWINGS

The invention will now be described by way of example with reference to the accompanying drawings, in which.

DETAILED DESCRIPTION

Figure 2:
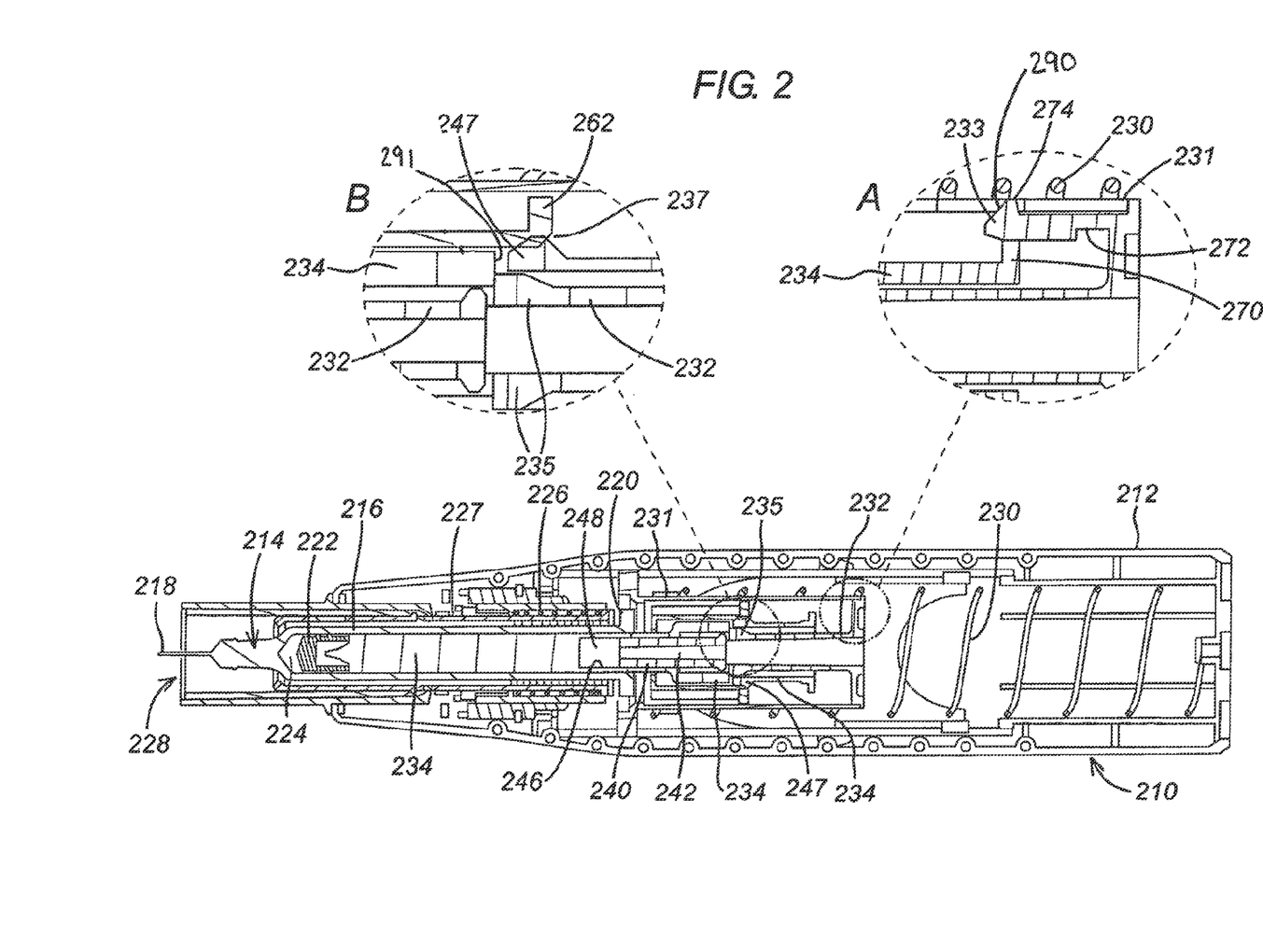
FIG. 2 is an embodiment of the present invention.

FIG. 2 shows an injection device 210 in which a housing 212 contains a hypodermic syringe 214. The syringe 214 is again of conventional type, including a syringe body 216 terminating at one end in a hypodermic needle 218 and at the other in a flange 220, and a rubber bung 222 that constraints a drug 224 to be administered within the syringe body 216. The conventional plunger that would normally be connected to the bung 222 and used to discharge the contents of the syringe 214 manually, has been removed and replaced with a multi-component drive element as will be described below.

Whilst the syringe illustrated is again of hypodermic type, this need not necessarily be so. As illustrated, the housing includes a return spring 226 that biases the syringe 214 from an extended position in which the needle 218 extends from aperture 228 in the housing 212, to a retracted position in which the hypodermic needle 218 is contained within the housing 212. The return spring 226 acts on the syringe 214 via a sleeve 227.

At the other end of the housing is a compression drive spring 230. Drive from the drive spring 230 this transmitted via the multi-component drive to the syringe 214 to advance it from its retracted position to its extended position and discharge its contents through the needle 218. The drive accomplishes this task by acting directly on the drug 224 and the syringe 214. Hydrostatic forces acting through the drug and, to a lesser extent, static friction between the bung 222 and the syringe body 216 initially ensures that they advance together, until the return spring 226 bottoms out or the syringe body 216 meets some other obstruction that retards its motion.

The multi component drive between the drive spring 230 and the syringe 214 again consists of three principal components. The drive sleeve 231 takes drive from the drive spring 230 and transmits it via the drive surface 290 to flexible latch arms 233 on a first drive element 232. These elements are shown in detail "A". The first drive element 232 in turn transmits drive via flexible latch arms 235 to drive surface 291 on a second drive element 234. These elements are shown in detail "B". As before, the first drive element 232 includes a hollow stem 240, the inner cavity of which forms a collection chamber 242. The second drive element 234 includes a blind for 246 that is open at one end to receive the stem 240 and closed at the other. As can be seen, the bore 246 and the stem 240 define a fluid reservoir 248, within which a damping fluid is contained.

A trigger (not shown) is provided at the middle of the housing 212 and, when operated, serves to decouple the drive sleeve 231 from the housing 212 allowing it to move relative to the housing 212 under the influence of the drive spring 230. The operation of the device is then as follows.

Initially, the drive spring 230 moves the drive sleeve 231, the drive sleeve 231 moves the first drive element 232 and the first drive element 232 moves the second drive element 234, in each case by acting through the flexible matching arms 233, 235. The second drive element 234 moves and, by virtue of static friction and hydrostatic forces acting through the drug 224 to be administered, moves the syringe body 216 against the action of the return spring 226. The return spring 226 compresses and the hypodermic needle 218 emerges from the exit aperture 228 of the housing 212. This continues until the return spring 226 bottoms out or the syringe body 216 meets some other obstruction that retards its motion. Because the static friction between the bung 222 and the syringe body 216 and the hydrostatic forces acting through the drug 224 to be administered are not sufficient to resist the full drive force developed by the drive spring 230, at this point the second drive element 234 begins to move within the syringe body 216 and the drug 224 begins to be discharged. Dynamic friction between the bung 222 and the syringe body 216 and hydrostatic forces acting through the drug 224 to be administered are, however, sufficient to retain the return spring 226 in its compressed state, so the hypodermic needle 218 remains extended.

Before the second drive element 234 reaches the end of its travel within the syringe body 216, so before the contents of the syringe have fully discharged, the flexible latch arms 235 linking the first and second drive elements 232, 234 reach a constriction 237. The constriction 237 is formed by a component 262 that is initially free to move relative to all other components, but that is constrained between the syringe flange 220 and additional flexible arms 247 on the second drive element 234. These additional flexible arms 247 overlie the flexible arms 235 on the first drive element 232, by means of which drive is transmitted to the second drive element 234. FIG. 4 illustrates the injection device 210 at the position where the additional flexible arms 247 are just making contact with the constriction 237 in the component 262.

The constriction 237 moves the additional flexible arms 247 inwards, aided by the bevelled surfaces on both, and the additional flexible arms 247 in turn move the flexible arms 235, by means of which drive is transmitted from the first drive element 232 to the second drive element 234, inwards from the position shown to a position at which they no longer engage the drive surface 291 and couple the first and second drive elements together. Once this happens, the first drive element 232 acts no longer on the second drive element 234, allowing the first drive element 232 to move relative to the second drive element 234.

Because the damping fluid is contained within a reservoir 248 defined between the end of the first drive element 232 and the blind bore 246 in the second drive element 234, the volume of the reservoir 248 will tend to decrease as the first drive element 232 moves relative to the second drive element 234 when the former is acted upon by the drive spring 230. As the reservoir 248 collapses, damping fluid is forced into the collection chamber 242. Thus, once the flexible latch arms 235 have been released, the force exerted by the drive spring 230 does work on the damping fluid, causing it to flow into the collection chamber 242, and also acts hydrostatically through the fluid and through friction between the first and second drive elements 232, 234, thence via the second drive element 234. Losses associated with the flow of the damping fluid do not attenuate the force acting on the body of the syringe to a great extent. Thus, the return spring 226 remains compressed and the hypodermic needle remains extended.

After a time, the second drive element 234 completes its travel within the syringe body 216 and can go no further. At this point, the contents of the syringe 214 are completely discharged and the force exerted by the drive spring 230 acts to retain the second drive element 234 in its terminal position and to continue to cause the damping fluid to flow into the collection chamber 142, allowing the first drive element 232 to continue its movement.

A flange 270 on the rear of the second drive element 234 normally retains the flexible arms 233 in engagement with the drive surface 290 of the drive sleeve 231. However, before the reservoir 248 of fluid is exhausted, the flexible latch arms 233 linking the drive sleeve 231 with the first drive element 232 move sufficiently far forward relative to the second drive element 234 that the flange 270 is brought to register with a rebate 272 in the flexible arms 233, whereupon it ceases to be effective in retaining the flexible arms 233 in engagement with drive surface 290 of the drive sleeve 231. Now, the drive sleeve 231 moves the flexible latch arms 233 inwards from the position shown to a position at which they no longer couple the drive sleeve 231 to the first drive element 232, aided by the bevelled latching surfaces 274 on the flexible arms 233. Once this happens, the drive sleeve 231 acts no longer on the first drive element 232, allowing them to move relative to each other. At this point, of course, the syringe 214 is released, because the forces developed by the drive spring 230 are no longer being transmitted to the syringe 214, and the only force acting on the syringe will be the return force from the return spring 226. Thus, the syringe 214 now returns to its retracted position and the injection cycle is complete.

The invention claimed is:

1. A releasable drive coupling comprising:
a first drive element having a first projecting flexible arm; and
a second drive element capable of sliding relative to the first drive element, wherein said first drive element is adapted to act on said second drive element, which is adapted to act on a driven element to impart drive thereto, the second drive element having:
a drive surface adapted to receive the first flexible arm, to allow axial loads to be transmitted from one drive element to the other; and
a second projecting flexible arm,
wherein the second flexible arm is configured to flex inwardly and is so positioned relative to the drive surface and the first flexible arm that inward flexing of the second flexible arm moves the first flexible arm inwardly to a point at which it is no longer received by the drive surface, at which point the first and second drive elements are free to slide relative to one another and the drive coupling is thus disengaged.

2. A coupling according to claim 1 in which the first and second flexible arms operate in compression to transmit axial loads from one drive element to the other.

3. A coupling according to claim 1 or claim 2 in which:
the first drive element is an inner drive element;
the first flexible arm projects outwardly from the inner drive element;
the second drive element is an outer drive element capable of sliding over the inner drive element;
the second flexible arm projects outwardly from the outer drive element; and
inward flexing of the second flexible arm causes it to flex the first flexible arm inwardly.

4. A coupling according to claim 3 in which the outer drive element has a bore in which the inner drive element is received.

5. A coupling according to claim 4 in which:
the inner drive element has a plurality of outwardly projecting, inner flexible arms; and
the outer drive element has a corresponding plurality of drive surfaces and a corresponding plurality of outwardly projecting, outer flexible arms.

6. A coupling according to claim 5 in which the outwardly projecting, inner flexible arms are substantially equidistantly spaced around the circumference of the inner drive element.

7. A coupling according to claim 6 comprising exactly two, diametrically opposite inner flexible arms.

8. A coupling according to claim 7 comprising exactly two, diametrically opposite outer flexible arms.

9. A coupling according to claim 5 in which the outwardly projecting, outer flexible arms are substantially equidistantly spaced around the circumference of the outer drive element.

10. An injection device comprising:
a releasable drive coupling according to claim 1;
an actuator acting upon one of the drive components; and
a decoupling component so arranged that, as the second drive element is advanced by the actuator, it flexes the second flexible arm inwardly, automatically disengaging the drive coupling.

11. An injection device according to claim 10:
a housing adapted to receive a syringe having a discharge nozzle, the housing including means for biasing the syringe from an extended position in which the discharge nozzle extends from the housing to a refracted position in which the discharge nozzle is contained within the housing;
an wherein said automatically releasable drive coupling is such that the first drive element is acted upon by the actuator and the second drive element acts upon the syringe to advance it from its retracted position to its extended position and discharge its contents through the discharge nozzle; and
the decoupling component automatically disengages the drive coupling when the drive elements have been advanced to a decoupling position.

12. An injection device according to claim 11, further comprising:
a release mechanism, activated when the first drive element has been advanced to a release position that is more advanced than the said decoupling position, and adapted to release the syringe from the action of the actuator, whereupon the biasing means restores the syringe to its retracted position.

13. An injection device according to claim 12 in which the release position is defined by the actuator interacting with the first drive element once the decoupling position has been reached, at which position the first drive element is restrained by the syringe against further movement and the second drive element is pushed into a recess on the first drive element.

14. An injection device according to claim 12 or 13, further comprising a second coupling, between the actuator and the first drive element, that prevents the actuator from moving relative to the first drive element until the release position has been reached.

15. An injection device according to claim 14 in which the second coupling comprises cooperating features of the actuator and the first drive element allowing the former to act upon the latter.

16. An injection device according to claim 12 or claim 13 in which the release mechanism is adapted to decouple the first drive element from the actuator once the said release position has been reached, thus releasing the syringe from the action of the actuator.

17. An injection device according to claim 10 in which the decoupling component comprising a channel through which the first and second drive elements pass when acted upon by the actuator, the channel being so arranged that, as the second drive element passes through it, it flexes the second flexible arm inwardly, automatically disengaging the drive coupling.

18. An injection device comprising:
a housing adapted to receive a syringe having a discharge nozzle, the housing including means for biasing the syringe from an extended position in which the discharge nozzle extends from the housing to a refracted position in which the discharge nozzle is contained within the housing;
an actuator;
first and second drive elements, of which the first is acted upon by the actuator and in turn acts upon the second, and the second acts upon the syringe to discharge its contents through the discharge nozzle, the first drive element being capable of movement relative to the second when the first is acted upon by the actuator and the second is restrained by the syringe;

of the actuator and the first drive element, one comprises a flexible arm that engages with a drive surface on the other, allowing the actuator to act upon the first drive element and preventing the former from moving relative to the latter; and the second drive element comprises a stop that prevents the flexible arm disengaging from the drive surface until the first drive element has been advanced to a release position relative to the second, whereupon the flexible arm disengages from the drive surface, allowing the actuator to move relative to the first drive element and thus releasing the syringe from the action of the actuator, whereupon the biasing means restores the syringe to its retracted position.

19. An injection device according to claim 18 further comprising a releasable coupling comprises cooperating features of the first and second drive elements that allow the first to act upon the second.

20. An injection device according to claim 19 in which the cooperating features include flexible arms on one of the drive elements that engage with a drive surface on the other.

21. An injection device according to claim 20 in which the coupling comprises a decoupling mechanism, activated when the drive elements have been advanced to a decoupling position and adapted to decouple the inner drive element from the outer, thus allowing the first drive element to move relative to the second.

22. An injection device according to claim 20 in which the flexible arms are biased toward a position at which they engage the drive surface and the decoupling component causes them to move against their bias, thus disengaging them from the drive surface.

23. An injection device according to claim 19, in which:
the releasable coupling comprises flexible arms on one of the drive elements that engage with a drive surface on the other; and
the decoupling component causes the flexible arms to move when a decoupling position is reached, by acting on an intermediate component, thus disengaging the flexible arms from the drive surface to allow the first drive element to move relative to the second.

24. An injection device according to claim 23 in which the intermediate component is a flexible component of the drive element upon which the said drive surface is to be found.

25. An injection device according to claim 18 in which the second drive element advances the syringe from its retracted position to its extended position.

26. An injection device according to claim 18 or claim 25 in which the flexible arm includes a detent and the stop is in register with the detent when the said release position is reached, thus allowing the flexible arms to flex.

27. An injection device comprising:
a housing adapted to receive a syringe having a discharge nozzle, the housing including means for biasing the syringe from an extended position in which the discharge nozzle extends from the housing to a refracted position in which the discharge nozzle is contained within the housing;
an actuator;
a drive, acted upon by the actuator and acting upon the syringe to discharge its contents through the discharge nozzle; and
of the actuator and the drive, one comprises a flexible arm that engages with a drive surface on the other, allowing the actuator to act upon the drive and preventing the former from moving relative to the latter;
a stop which prevents the flexible arm from disengaging from the drive surface until the drive has been advanced to a release position, whereupon the flexible arm disengages from the drive surface, allowing the actuator to move relative to the drive and thus releasing the syringe from the action of the actuator, whereupon the biasing means restores the syringe to its retracted position; and
in which the flexible arm is biased toward a position at which it engages the drive surface and the action of the actuator causes it to move against its bias, thus disengaging it from the drive surface.

28. An injection device according to claim 18 or 27, in which the action of the actuator tends to disengage the flexible arm from the drive surface, but is prevented from doing so until the said release position has been reached.

29. An injection device according to claim 28 in which the said one of the actuator and the first drive element comprises a plurality of such flexible arms.

30. An injection device according to claim 18 or claim 27 in which the said one of the actuator and the first drive element is the first drive element.

* * * * *